United States Patent [19]

Miller

[11] Patent Number: 4,780,454

[45] Date of Patent: Oct. 25, 1988

[54] ANTI-PROTOZOAL TREATMENT

[75] Inventor: Richard L. Miller, Raleigh, N.C.

[73] Assignee: Burroughs Wellcome Co., Research Triangle Park, N.C.

[21] Appl. No.: 81,476

[22] Filed: Aug. 4, 1987

Related U.S. Application Data

[63] Continuation of Ser. No. 876,234, Jun. 19, 1986, abandoned.

[51] Int. Cl.⁴ ............................................. A61K 31/70
[52] U.S. Cl. ......................................... 514/51; 514/50
[58] Field of Search ....................... 514/50, 51; 536/23

[56] References Cited

PUBLICATIONS

De Clercq et al.; Biochemical Pharmocology, vol. 29, pp. 1849–1851 (1981).
C. A. De Clercq et al. vol. 93 (1980), 93:215,266x, 1971–1981 Formula Index 4615F.

Primary Examiner—Allen J. Robinson
Attorney, Agent, or Firm—Donald Brown

[57] ABSTRACT

3'-Azido-3'-deoxythymidine is disclosed as an effective treatment for giardiasis.

15 Claims, No Drawings

ANTI-PROTOZOAL TREATMENT

This is a continuation of application Ser. No. 876,234, filed June 19, 1986, now abandoned.

The present invention relates to the treatment of giardiasis with 3'-azido-3'-deoxythymidine or its pharmaceutically acceptable basic salts.

Giardiasis in human beings is caused by *Giardia lamblia* (also called *Giardia intestinalis*), a flagellate protozoan which is found in almost all parts of the world. This parasite, considered to be the leading protozoan cause of diarrhea among travelers, is predominently water-borne, but person-to-person and food-borne transmission also occur. Internationally it is one of the major causes of diarrheal disease in infants and young children and thus contributes significantly to the excessive morbidity and mortality in children of developing countries.

Domestic and certain wild animals are also susceptible to giardiasis. *G. canis* is the species infecting dogs, although crossover infections have been reported between human beings and dog and between beaver and human beings.

We have now found that effective treatment of giardial infections in mammals may be accomplished by the administration to infected mammals, especially human beings, of the compound of formula (I)

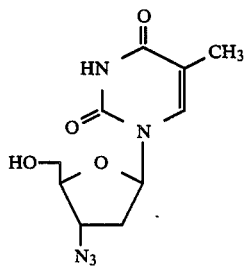

(I)

Pharmaceutically acceptable salts which are especially preferred for therapeutic use are salts of alkali metals such as sodium and potassium, alkaline earth metals such as calcium and magnesium and ammonium salts such as tetralkylammonium salts. Alkyl may be straight or branched chain and may contain 1-5 carbon atoms and is preferably methyl or ethyl.

The salts of the compound convert to the compound per se after being administered to the human and are thus prodrugs. The compound 3'-azido-3'-deoxythymidine penetrates into the Giardia lamblia cells after contacting same and is converted by the giardial enzymes to the monophosphate thereof. The monophosphate is then converted by the giardial enzymes to the diphosphate of the compound of formula (I) and ultimately to the triphosphate of the compound of formula (I).

All prodrugs (precursors) are administered to a human in an amount sufficient to generate an effective amount of the compound which contacts the *Giardia lamblia* and interacts with it (e.g., prevents replication thereof).

Thus, the compound of formula (I) can be said to be a prodrug after entering the *Giradia lamblia* cells since it is an intermediate (precursor) to the mono-, di-, and triphosphate thereof.

It is believed that the mono-, di-, and triphosphates of the compound of formula (I) can also be said to be prodrugs since they would invariably (at least in part) by hydrolyzed in the body to 3'-azido-3'-deoxythymidine which is then taken up by the giardial cells.

As another feature of this invention, there is also disclosed the method of administering to a human in need thereof the 5'-mono-, 5'-di-, or 5'-triphosphate of the compound of formula (I) or their pharmaceutically acceptable base salts (i.e., alkali metal, alkaline earth or ammonium salt) to treat giardiasis. The 5'-mono-, 5'-di-, and 5'-triphosphates of 3'-azido-3'-deoxythymidine are of the formulas (II), (III) and (IV) respectively.

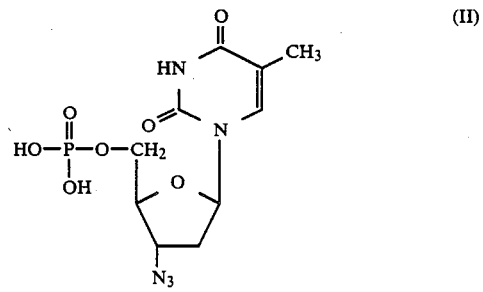

(II)

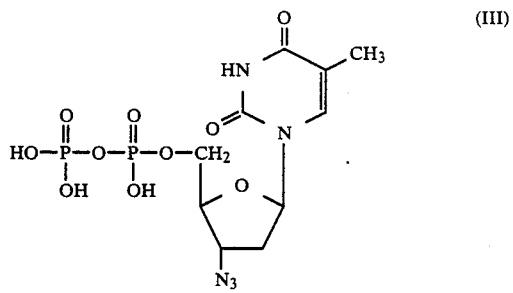

(III)

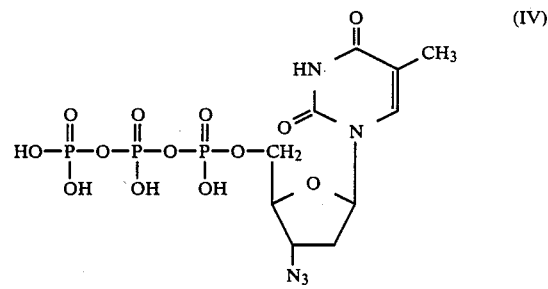

(IV)

The present invention also discloses compounds of formulas (I), (II), (III) and (IV) and their appropriate salts for use in the treatment of giardiasis, as well as the use of such compounds in the preparation of pharmaceutical formulations for the treatment of such condition. The above mentioned pharmaceutically acceptable salts may be prepared in a conventional manner, e.g., treatment of the compound with an appropriate base.

The compound of formula (I) has been disclosed in various publications as having activity against retroviruses such as HTLV-III, intra alia, and gram negative bacteria. The compound of formula (I) may be prepared in conventional manner, for example as described by Horwitz, et al., *J. Org. Chem.* 29 (1914) 2076.

As used herein "effective unit dosage" or "effective unit dose" means a dose containing a predetermined amount of a compound of formula (I), its pharmaceutically acceptable salts, its 5'-mono-, 5'-di-, or 5'-triphosphate or a pharmaceutically acceptable salt thereof sufficient to be effective against the giardial organisms in vivo. Pharmaceutically acceptable carriers are materials useful for the purpose of administering the medicament, and may be solid, liquid or gaseous materials which are otherwise inert and medically acceptable and are compatible with the active ingredients.

The pharmaceutical compositions of this invention, for the treatment of giardial infections, may be given orally, topically in the mouth (e.g., buccal or sublingual), parenterally, as a suppository or as an aerosol. The compositions are administered at dose levels of the compound of formula (I), its 5'-mono-, 5'-di-, or 5'-triphosphate, or a pharmaceutically acceptable salt thereof (hereinafter thereof referred to as active ingredients), calculated as the free base, of about 0.1 to about 100 mg per kg, preferably about 1 to about 40 mg per kg, and most preferably about 2 to about 20 mg per kg of mammal body weight per day, and are used in human beings in unit dosage form, administered 1 to about 4 times per day in an amount of about 2 to about 250 mg per unit dose.

While it is possible for the active ingredients to be administered alone it is preferable to resent them as pharmaceutical formulations. The formulations, both for veterinary and for human use, of the present invention comprise at least one active ingredient, as above defined, together with one or more pharmaceutical carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical in the mouth (e.g., buccal or sublingual), or parenteral (including subcutaneous, intramuscular, intravenous and intradermal) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredients with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, such active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acadia; and mouthwashes comprising the active ingredient in a suitable liquid carrier. Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient. For parenteral administration the compounds of formula (I) or their pharmaceutically acceptable salts may be presented in aqueous solution in a concentration of from about 0.1 to 10%, preferably about 0.1 to about 5%, most preferably about 0.2% w/v.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising the active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by other desired route.

For oral administration the compositions can be in the form of a tablet, granule, drench, paste, cachet, capsule or feed supplement. Granules may be made by the well known techniques of wet granulation, precompression or slugging. They can be administered to animals in an inert liquid vehicle so as to form a drench, or in a suspension with water or oil base. Preferably further accessory ingredients such as a dispensing agent are included. These formulations preferably contain from 15 to 85% of the active ingredient.

A paste may be formulated by suspending the active ingredient in a liquid diluent. A stiffening or thickening agent may be included together with a wetting agent or a humectant if the liquid diluent is water. If an emulsion paste is needed then one or more surface active agents should desirably be included. From 25 to 80% by weight of these paste formulations may comprise the active ingredient.

In feed supplements the active ingredient is generally present in large amounts relative to the accessory ingredients, and the supplements may be added directly or after intermediate blending or dilution. Examples of accessory ingredients for such formulations include solid, orally ingestible carriers such as corn meal, soya flour, wheat shorts, soya grits, edible vegetable materials and fermentation residues. The active ingredient is usually incorporated in one or more of the accessory ingredients and intimately and uniformly dispersed by grinding, tumbling or stirring with conventional apparatus. Formulations containing 1 to 90% by weight of the active ingredient are suitable for adding to feeds.

Example 1 Tablet

| Compound of formula (I) | 10 mg |
|---|---|
| Lactose | 134 mg |
| Polyvinylpyrrlidone | 5 mg |
| Corn starch | 50 mg |
| Magnesium stearate | 1 mg |

The above formulation is sufficient to comrise one 200 mg tablet. The tablet may be enteric coated to prevent disintegration in the stomach.

Example 2 Capsule

| Compound of formula (I) | 10 mg |
|---|---|
| Lactose | 50 mg |
| Corn starch | 138 mg |
| Magnesium stearate | 2 mg |

A two-piece, hard shell, clear or opaque gelatin capsule is filled with the above formulation to a fill weight of 200 mg. The capsule may be enteric coated to prevent disintegration in the stomach.

Example 3 Syrup

| Compound of formula (I) | 10 mg |
|---|---|
| Lactose | 3 mg |
| Glycerine | 1 mg |
| Flavoring agent | q.s. |
| Distilled water | q.s. to 5.0 ml |

The above formulation comprises a one teaspoon, single dose of a syrup containing a compound of this invention.

Example 4 Suppository

| Compound of formula (I) | 10 mg |
|---|---|
| Cocoa butter | q.s. to 2.0 g |

The cocoa butter is heated to melting and the compound of formula (I) dispersed therein by thorough mixing. The mass is then formed into suppositories weighing 2.0 g each.

Example 5 Anti-Giardial Activity

*Giardia lamblia* WB strain (ATCC 30957) was grown in TYI-S-33 medium [D. B. Kiester, Transactions of the Royal Society of Tropical Medicine and Hygiene, Vol. 27, No. 4, p. 487–488 (1983)]. Compound of formula (I) was added to portions of the logarithmically growing culture to give concentrations of the compound ranging from about 1 $\mu$M to 17 $\mu$M. The ED$_{50}$ values were determined after incubation at 37° C. for 45.5 and 69.5 hr to be 7 $\mu$M at both time periods.

I claim:

1. A method for treating giardial infection of a mammal in need of treatment comprising the administration to said mammal of an effective, non-toxic antigiardial amount of a compound of formula (I)

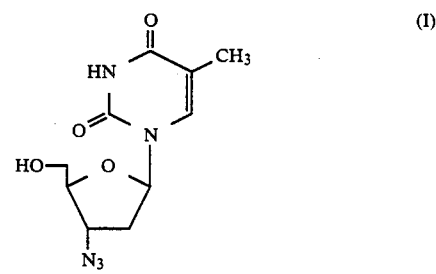

or a pharmaceutically acceptable salt thereof.

2. A method according to claim 1 wherein said mammal is a human being.

3. A method according to claim 1 wherein said compound is administered in association with a pharmaceutically acceptable carrier therefor.

4. A method according to claim 3 wherein said compound is in a form suitable for oral, rectal or parenteral administration.

5. A method according to claim 4 wherein said compound is in unit dosage form.

6. A method according to claim 1 which comprises the administration to said mammal of from 1 to 100 mg per kg of body weight per day of said compound.

7. A method according to claim 6 wherein from 2 to 50 mg per kg of body weight per day of said compound is administered to said mammal.

8. A method according to claim 6 wherein from 3 to 40 mg per kg of body weight per day of said compound is administered to said mammal.

9. A method for treating giardial infection of a mammal in need of said treatment thereof comprising the administration of said mammal of an effective, non-toxic antigiardial amount of a compound of formula (I)

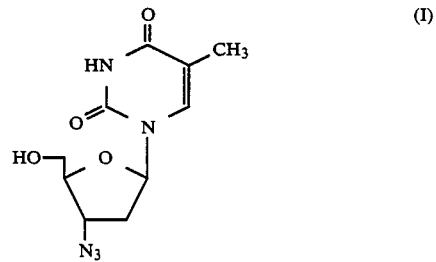

or its 5'-mono-, 5'-di-, or 5'-triphosphate or a pharmaceutically acceptable salt thereof.

10. A method according to claim 9 wherein said mammal is a human being.

11. A method according to claim 9 wherein said 5'-monophosphate is administered.

12. A method of treating a *Giardia lamblia* infection in a human suffering from same which comprises internally administering an effective *Giardia lamblia* treatment amount of the compound 3¹-azido-3¹-deoxythymidine or a pharmaceutically acceptable salt thereof to said human.

13. The method of claim 12 in which a tablet or capsule containing the compound or salt is orally administered.

14. The method of claim 12 in which an injectable preparation containing the compound or salt is parenterally adminstered.

15. The method of claim 12 in which 3'-azido-3'-deoxythymidine is administered.

* * * * *